(12) United States Patent
Mazar et al.

(10) Patent No.: US 10,285,644 B2
(45) Date of Patent: May 14, 2019

(54) PATIENT WORN SENSOR ASSEMBLY

(71) Applicant: Vios Medical, Inc., St. Paul, MN (US)

(72) Inventors: Scott Mazar, Woodbury, MN (US);
Amit Patel, Woodbury, MN (US);
Brandon J. LaPlante, Minneapolis, MN (US)

(73) Assignee: Vios Medical, Inc., St. Paul, MN (US)

( * ) Notice: Subject to any disclaimer, the term of this patent is extended or adjusted under 35 U.S.C. 154(b) by 460 days.

(21) Appl. No.: 15/019,431

(22) Filed: Feb. 9, 2016

(65) Prior Publication Data
US 2016/0228060 A1    Aug. 11, 2016

Related U.S. Application Data

(60) Provisional application No. 62/113,688, filed on Feb. 9, 2015.

(51) Int. Cl.
*A61B 5/00* (2006.01)
*A61B 5/0408* (2006.01)
*A61B 5/0205* (2006.01)
*A61B 5/024* (2006.01)

(52) U.S. Cl.
CPC ........ *A61B 5/6833* (2013.01); *A61B 5/04085* (2013.01); *A61B 5/0205* (2013.01); *A61B 5/02055* (2013.01); *A61B 5/02438* (2013.01); *A61B 2560/0412* (2013.01); *A61B 2562/225* (2013.01)

(58) Field of Classification Search
None
See application file for complete search history.

(56) References Cited

U.S. PATENT DOCUMENTS

| 6,076,002 A | 6/2000 | Cartmell et al. |
| 6,141,575 A | 10/2000 | Price |
| 6,605,046 B1 * | 8/2003 | Del Mar ............ A61B 5/04085 600/507 |
| 7,249,036 B2 | 7/2007 | Bayne |
| 7,512,449 B2 | 3/2009 | Lang et al. |
| 7,739,126 B1 | 6/2010 | Cave et al. |

(Continued)

FOREIGN PATENT DOCUMENTS

WO    2013/130545    9/2013

OTHER PUBLICATIONS

International Preliminary Report on Patentability in International Application No. PCT/US2016/017151, dated Aug. 15, 2017, 9 pages.

(Continued)

*Primary Examiner* — Brian T Gedeon
(74) *Attorney, Agent, or Firm* — Fish & Richardson P.C.

(57) ABSTRACT

A patient worn sensor assembly for detecting, recording, and communicating patient vital signs includes several structural features that can provide increased signal quality, reduction in signal noise, increased patient comfort, increased reliability, and increased adhesion to a patient's skin. The patient worn sensor can track vital sign information such as blood pressure, body temperature, respiratory rate, blood oxygenation, heart rhythm (via ECG), heart rate, blood glucose level, and hydration (bio-impedance) levels. The sensor can also track and record additional information about patients, including patient movement, activity, and sleep patterns.

20 Claims, 8 Drawing Sheets

(56) References Cited

U.S. PATENT DOCUMENTS

| | | |
|---|---|---|
| 7,818,050 B2 | 10/2010 | Rapoport et al. |
| 8,000,978 B2 | 8/2011 | Wager et al. |
| 8,117,046 B2 | 2/2012 | Bayne |
| 8,160,673 B2 | 4/2012 | Furtinger |
| 8,340,981 B1 | 12/2012 | Cave |
| 8,504,291 B2 | 8/2013 | Bayne |
| 8,630,699 B2 | 1/2014 | Baker et al. |
| 8,639,528 B1 | 1/2014 | Cave |
| 8,751,160 B2 | 6/2014 | Bayne |
| 8,768,726 B1 | 7/2014 | Cave |
| 8,786,402 B2 | 7/2014 | Barnes |
| 2009/0076364 A1 | 3/2009 | Libbus et al. |
| 2010/0081913 A1 | 4/2010 | Shinbo et al. |
| 2012/0088999 A1 | 4/2012 | Bishay et al. |
| 2013/0030825 A1 | 1/2013 | Bagwandeen et al. |
| 2013/0035946 A1 | 2/2013 | Ratan et al. |
| 2013/0079618 A1 | 3/2013 | Sandmore et al. |
| 2013/0197942 A1 | 8/2013 | Chiu et al. |
| 2013/0297350 A1 | 11/2013 | Gross et al. |
| 2014/0288961 A1 | 9/2014 | Bayne |
| 2014/0337055 A1 | 11/2014 | Barnes |
| 2015/0310173 A1 | 10/2015 | Coney |
| 2015/0332011 A1 | 11/2015 | Ting et al. |
| 2016/0239626 A1 | 8/2016 | Buckley et al. |
| 2016/0253457 A1 | 9/2016 | Anumolu et al. |
| 2016/0314277 A1 | 10/2016 | Korhonen et al. |
| 2017/0017767 A1 | 1/2017 | Flower et al. |

OTHER PUBLICATIONS

Extended European Search report in Application No. 16749710.6, dated Nov. 2, 2017, 9 pages.
EPC Communication in European Patent Application No. 16749710.6, dated May 9, 2018, 7 pages.

\* cited by examiner

PATIENT WORN SENSOR ASSEMBLY

CROSS-REFERENCE TO RELATED APPLICATIONS

This application claims the benefit of U.S. Provisional Application Ser. No. 62/113,688, filed Feb. 9, 2015. The disclosure of the prior application is considered part of (and is incorporated by reference in) the disclosure of this application.

FIELD OF TECHNOLOGY

The present disclosure is directed toward patient monitoring devices and systems that include an electrode assembly that, in use, is temporarily affixed or adhered to the skin of a patient.

BACKGROUND

Many different types of patient monitoring systems require a direct electrical interface to the skin of a patient. In some applications, the direct electrical interface to the patient's skin is for sensing electrical information present at that skin location, while in other applications, the direct electrical interface is for injecting an electrical current signal at that skin location. One example of a device with a skin electrical interface is a patient-worn sensor device that, among other capabilities, may collect patient electrocardiogram ("ECG") information sensed at the skin of the patient and wirelessly transmit data indicative of the collected ECG information for receipt by another system such as a hospital, clinic or home-based monitoring system. In this wearable ECG sensor device example, the device typically includes firstly an adhesive electrode assembly with multiple individual electrodes wherein the assembly is adapted to be attached to the patient's skin, and secondly a sensor assembly that includes all of the sensing, processing and communication electronics and a power supply for a self-contained sensor-transmitter device. In this case, the electrode assembly provides the direct electrical interface and adhesion to the patient's skin as well as a platform to which the sensor assembly connects and is supported.

Another class of skin electrode assemblies are adapted to be connected by an electrical lead (or in other words, a long wire) to a separate monitoring system, and are intended to be used with the patient "tethered" to the monitoring system. In this electrode assembly example, the patient-worn assembly typically includes an electrode assembly with one or more electrodes adapted to be adhered to the patient's skin and an associated connector assembly with an associated number of contacts to the electrodes of the electrode assembly. The connector assembly is adapted such that a monitoring system lead may be connected to it to provide an electrical connection between the one or more electrodes of the electrode assembly and the sensing and processing circuitry of the separate monitoring system.

SUMMARY

A patient worn sensor assembly for detecting, recording, and communicating patient vital signs includes several structural features that can provide increased signal quality, reduction in signal noise, increased patient comfort, increased reliability, and increased adhesion to a patient's skin. The patient worn sensor can track vital sign information such as blood pressure, body temperature, respiratory rate, blood oxygenation, heart rhythm (via ECG), heart rate, blood glucose level, and hydration (bio-impedance) levels. The sensor can also track and record additional information about patients, including patient movement, activity, and sleep patterns.

The patient worn sensor can include a sensor housing for storing electrical components for processing signals received from and detected in association with the patient and for transmitting information to other devices (e.g., bed side monitors, tablet devices, mobile phones, central processing servers, etc.). The patient worn sensor can further include an adherent electrode pad designed to affix to the chest of the patient or to another portion of the patient's body. Electrodes included as part of the adherent electrode pad can be configured to contact electrical leads of the sensor housing to convey signals from the patient to the electrical components within the sensor housing of the patient worn sensor. Each of the electrodes of the adherent electrode pad can further include hydrogels for contacting the skin of the patient and collecting vital sign information. In some implementations, the sensor housing can include snap connectors for engaging electrodes of the adherent electrode pad and for securing the adherent electrode pad to the sensor housing. In some implementations, the adherent electrode pad can be disposable. The disposable adherent electrode pad can be periodically removed and replaced with a fresh adherent electrode pad while allowing many of the components of the patient worn sensor (such as the components of the sensor housing) to be continually reused.

The sensor housing of the sensor can include stabilizing boots that surround each of the electrical leads extending from the sensor housing. The stabilizing boots can absorb shock caused by motion of the patient in order to provide better signal quality. For example, the stabilizing boots can reduce the negative effects on signal quality caused by motion of the electrodes of the electrode pad with respect to each other caused by motion of the patient. In some implementations, one of the electrical leads of the sensor housing serves as a drive electrical contact (providing electrical current) and a second electrode serves as an extraction electrode for receiving the electrical current while one or more other electrodes are detecting electrodes for detecting changes in electrical signals within the patient's body. In some implementations, the stabilizing boot surrounding the drive electrical contact can be more rigid than the stabilizing boots surrounding the other electrical contacts, thereby restricting the movement of the drive electrical contact with respect to the patient more than the movement of the other electrical contacts. In some implementations, the drive electrical contact (and therefore, the more rigid stabilizing boot) can be positioned in a relatively central location of a surface of the sensor housing and/or the other electrical leads. For example, the electrical leads can form a clover-like pattern with the drive electrical lead positioned at the center of the clover-like pattern.

The adherent electrode pad can include a stabilizing sheet that contacts each of the electrodes embedded within the electrode pad. The stabilizing sheet can, for example, encircle a portion of each electrode. The electrodes can, for example, extend through a flexible layer (e.g., a foam layer or a layer made from another suitably flexible material) and the stabilizing sheet can be parallel to and in contact with the flexible layer. The stabilizing sheet can restrict lateral movement of the electrodes with respect to each other in X and Y directions while allowing for a degree of movement of the electrodes with respect to each other in the Z direction.

The flexible layer of the adherent electrode pad can also be configured to form a tented configuration with respect to the electrodes and their respective hydrogels. For example, the electrodes and hydrogels can be affixed to the flexible layer such that when the adherent electrode pad is attached to a patient's skin, air pockets are formed around the hydrogels between the flexible layer and the patient's skin. The air pockets can serve as collection areas for air bubbles formed between the patient's skin and the flexible layer to escape and can also serve as areas for sweat from the patient's skin to collect while reducing interference with the contact between the hydrogels and the patient's skin.

In general, one innovative aspect of the subject matter described in this specification can be embodied in a system that includes an electrode assembly for contact with a patient. The electrode assembly can include an elastic layer that is substantially larger along an X-axis and a Y-axis in comparison to a Z-axis of the elastic layer; a plurality of electrodes, a portion of each electrode of the plurality of electrodes extending at least partially through the elastic layer; and a stabilizing sheet positioned between at least a portion of each electrode and the elastic layer, the stabilizing sheet configured to restrict movement of the plurality of electrodes relative to each other along the direction of the X-axis and the direction of the Y-axis. A portion of each electrode can extend through the stabilizing sheet.

These and other embodiments can each optionally include one or more of the following features. The plurality of electrodes can include a central electrode and two or more peripheral electrodes. The one or more peripheral electrodes can be arranged substantially equidistantly from the central electrode. The two or more peripheral electrodes can include four electrodes with a distance between each adjacent pair of peripheral electrodes being substantially the same. The first surface area of a first plane of the stabilizing sheet defined by the X-axis and the Y-axis can be less than a second surface area of a second plane of the elastic layer defined by the X-axis and the Y-axis. The stabilizing sheet can include or be manufactured from label stock. The stabilizing sheet can be substantially clover shaped. The stabilizing sheet can restrict the elastic layer from being stretched in the direction of the X-axis and in the direction of the Y-axis. The elastic layer can be a foam layer such as, for example, foamed polyethylene.

In general, another innovative aspect of the subject matter described in this specification can be embodied in a system that includes an electrode assembly for contacting a patient. The electrode assembly can include an elastic layer; one or more electrodes, a portion of each of the one or more electrodes extending at least partially through the elastic layer; and one or more gel contacts, each of the one or more gel contacts affixed to an electrode of the one or more electrodes, each of the gel contacts positioned such that when the elastic layer is placed in contact with the skin of a patient, an air pocket at least partially surrounding the gel contact is formed, the air pocket being at least partially defined by the gel contact, the elastic layer, and the patient's skin.

These and other embodiments can each optionally include one or more of the following features. Each of the gel contacts can be positioned to form an additional air pocket, the additional air pocket can be at least partially defined by the gel contact, the electrode to which the gel contact is affixed, and the elastic layer. The one or more electrodes can include a plurality of electrodes. The electrode assembly can further include a stabilizing sheet positioned between at least a portion of each electrode and the elastic layer. The stabilizing sheet can be configured to restrict movement of the plurality of electrodes relative to each other along the direction of the X-axis and the direction of the Y-axis. A portion of each electrode can extend through the stabilizing sheet. The stabilizing sheet can restrict the elastic layer from being stretched in the direction of the X-axis and in the direction of the Y-axis.

In general, another innovative aspect of the subject matter described in this specification can be embodied in a system that includes a patient monitoring device for use with an electrode assembly configured to be applied to the skin of a patient. The patient monitoring device can include an electronics assembly having one or more extending contacts, each of the one or more extending contacts configured to releasably couple to an electrode of the electrode assembly; and one or more stabilizing boots, each of the one or more stabilizing boots encircling one of the one or more extending contacts.

These and other embodiments can each optionally include one or more of the following features. Each of the one or more stabilizing boots can be configured to allow for a greater degree of movement in a Z-axis direction than in X-axis and Y-axis directions of the electronics assembly relative to the patient. The one or more stabilizing boots can include a first stabilizing boot constructed of a material having a higher level of rigidity than the other stabilizing boots of the one or more stabilizing boots. The first stabilizing boot can have a substantially central position relative to the other stabilizing boots of the one or more stabilizing boots. The first stabilizing boot can restrict movement of the sensor assembly relative to the patient in the Z-axis to a greater degree than the other stabilizing boots of the one or more stabilizing boots. The one or more stabilizing boots can include five stabilizing boots and the first stabilizing boot can be equidistantly encircled by four other stabilizing boots. Each of the one or more stabilizing boots can at least partially encircle a portion of an electrode of the electrode assembly when the device is coupled to the electrode assembly.

Various other functions and benefits of such a sensor assembly will be apparent from the foregoing detailed description and claims.

DETAILED DESCRIPTION

Figure 1:
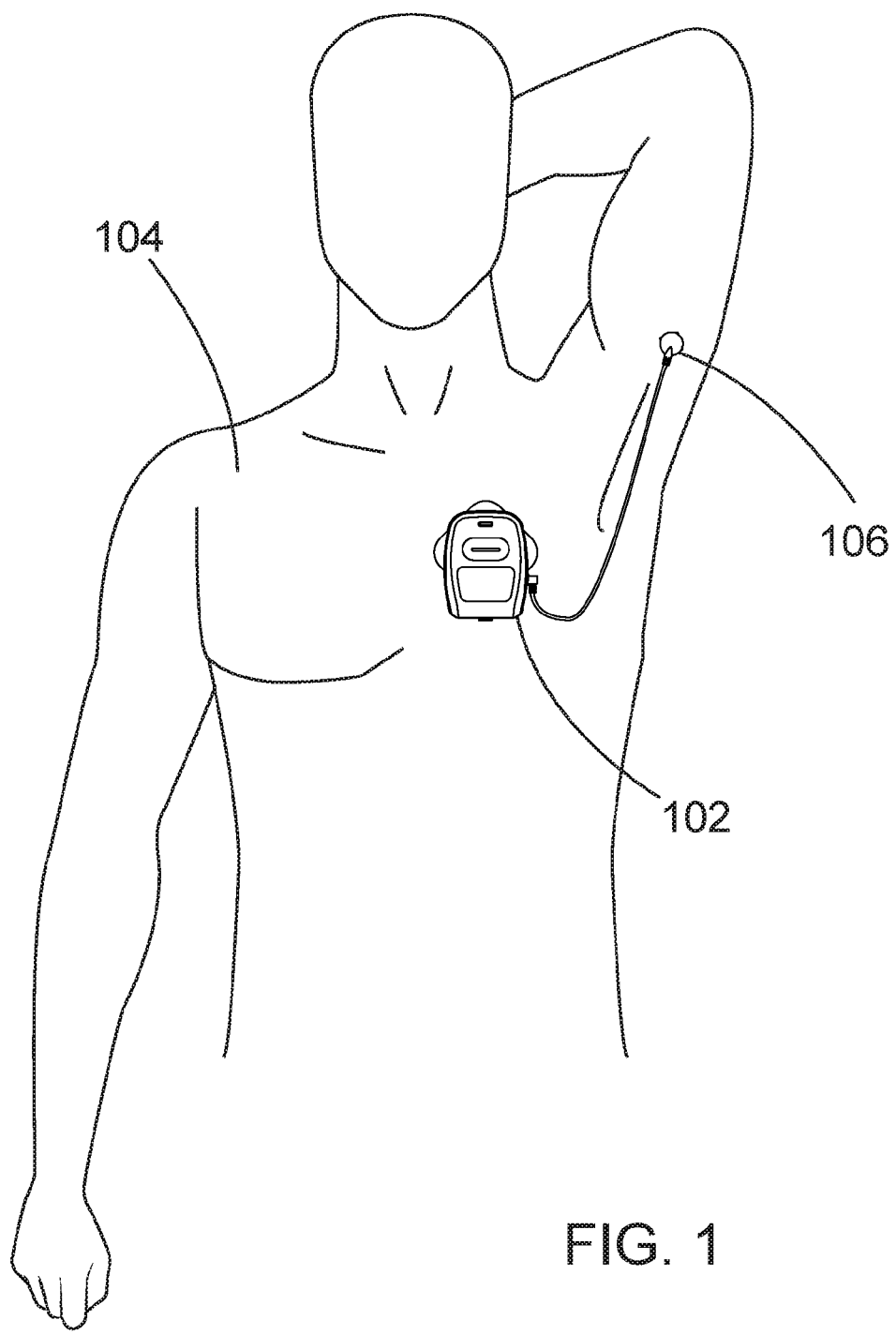
FIG. 1 shows an example patient worn sensor in contact with a patient.

FIG. 1 shows an example patient worn sensor 102 affixed to a patient 104. In the example shown, the patient worn sensor 102 is attached to the chest of the patient 104, however in other embodiments the patient worn sensor 102 can be affixed to one or more other areas on the patient 104's body. The patient worn sensor 102 is configured to detect and record various vital signs and other information for the patient 104 or for another patient with which the patient worn sensor 102 is in contact. The patient worn sensor 102 can include several adherent electrodes for contacting the skin of the patient 104 to record various vital signs for the patient, including heart rhythm (via ECG) and heart rate. The patient worn sensor 102 can be, for example, a 6-lead ECG sensor having I, II, III, aVL, aVR, and aVF leads. Other vital signs that can be monitored by the patient worn sensor 102 can include blood pressure, body temperature, respiratory rate, blood oxygenation, blood glucose level, hydration levels and perspiration. In some implementations, the patient worn sensor 102 can include a sensor housing for storing electrical components for processing signals received from and detected in association with the patient and for transmitting information to other devices. The patient worn sensor 102 can further include an adherent electrode pad designed to affix to the chest of the patient 104. Electrodes included as part of the adherent electrode pad can be configured to contact electrical leads of the sensor housing to convey signals from the patient 104 to the electrical components within the patient worn sensor 102. In some implementations, the sensor housing can include snap connectors for engaging electrodes of the adherent electrode pad and for securing the adherent electrode pad to the sensor housing. In some implementations, the adherent electrode pad can be disposable. The disposable adherent electrode pad can be periodically removed and replaced with a fresh adherent electrode pad while allowing many of the components of the patient worn sensor 102 to be continually reused. In some implementations, the electrode pad of the patient worn sensor 102 is not designed to be disposable.

The electrode pad of the patient worn sensor 102 is configured to adhere to the skin of the patient 104 and provide mechanical support for the sensor housing of the patient worn sensor 102. The electrode pad can, for example, include an elastic layer, such as a foam layer or a layer made from another suitably elastic material. The foam layer can be, for example, medical grade polyethylene foam or polyurethane foam. The elastic layer can be coated with an adhesive coating for contacting and affixing to the skin of the patient 104. The electrode pad includes electrodes for detecting various vital sign signals that can be processed by electronic circuitry of the patient worn sensor 102, or a computing device in communication with the patient worn sensor 102, to identify and track patient vital signs. Each electrode of the patient worn sensor 102 can include a hydrogel layer for contacting the skin of the patient and collecting vital sign information. Hydrogel layers can be positioned over metal portions of the electrodes to provide electrical conductivity between the electrodes and the skin of the patient 104. In some implementations, the electrode pad is removed from the patient worn sensor 102 and replaced on a regular basis (e.g., every three days) to ensure that sufficient contact with the patient's skin is maintained while keeping the contact site clean. The other components of the patient worn sensor 102 (contained within the sensor housing) can be continually reused with the electrode pad being replaced. The permanent components of the patient worn sensor 102 can additionally be reused for different patients, while the electrode pad is replaced when the patient worn sensor 102 is transferred from one patient to another.

The patient worn sensor 102 can also include sensors for detecting bio-impedance in order to monitor hydration levels, body fat levels, or other fluid levels for the patient 104. In some implementations, the patient worn sensor 102 can include electronics for processing and analyzing vital sign information and other information collected from the patient 104. In some implementations, the patient worn sensor 102 and/or other patient worn sensors collect raw, pre-processed information which is then transmitted to other portions of the system 100 for further processing and analysis.

In some implementations, the patient worn sensor 102 includes a temperature sensor 106 that extends from a main body of the patient worn sensor 102 to underneath the patient 104's armpit for monitoring, tracking, and recording body temperature for the patient 104. The temperature sensor 106 can include both reusable portions and temporary/disposable portions. For example, the temperature sensor 106 can include a disposable contact for affixing to the patient 104's skin under the patient 104's armpit. The temperature sensor 106 can, for example, further include permanent portions that include temperature sensing portions, circuitry for interpreting and processing temperature data received from the patient, and a cable running from the main body of the patient worn sensor 102 around the chest of the patient 104 to the patient 104's armpit. In some implementations, rather than including functionality for interpreting temperature data collected from the patient 104, the temperature sensor 106 can collect raw data that is processed by circuitry contained within the main housing of the patient worn sensor 102 or other computing devices in communication with the patient worn sensor 102. In some implementations, temperature measurements for a patient can be collected using an ear temperature sensor.

In some implementations, the patient 104 can additionally be outfitted with a wrist sensor. The wrist sensor can be used to track and record blood pressure and blood oxygenation (SpO2) for the patient 104. The wrist sensor can communicate vital sign data collected from the patient to the patient worn sensor 102, or can bypass the patient worn sensor 102 can communicate information directly to another computing device. As with the patient worn sensor 102, the wrist sensor can include both reusable and disposable portions. For example, the wrist sensor can include a reusable housing and circuitry for processing signals received from the patient 104 and a disposable portion for contacting the skin of the patient 104. In some implementations, the wrist sensor includes a finger sensor that extends from the wrist sensor and engages one or more fingers of the patient 104. The finger sensor can be used, for example, to measure blood oxygenation (SpO2) for the patient 104. In some implementations, rather than being located at the wrist of the patient 104, the wrist sensor can take the form of an upper arm sensor that is located at the upper arm (above the elbow) of the patient 104. The upper arm sensor can be used, for example, to measure blood pressure for the patient 104.

In some implementations, the patient worn sensor 102 includes one or more accelerometers for detecting and recording patient motion, activity, position, and posture. For example, an accelerometer included within the patient worn sensor 102 can track patient activity to allow a caregiver to determine if the patient 104 is receiving a sufficient level of daily exercise, or if the patient 104 is engaging in too much activity for the current physical condition of the patient 104. The accelerometer can also be used to determine if the patient 104 has fallen, or if the patient 104 has been motionless for a specified period of time. The accelerometer can also be used to track patient sleep patterns, or to track the posture of the patient 104 to allow caregivers to provide recommendations for how the patient 104 can better position himself when seated, lying, standing, etc. The accelerometer could additionally provide information to caregivers that can be used to determine if the patient 104 is engaging in activities or habits that can increase the risk of re-injury or of developing complications.

The patient worn sensor 102 can also include circuitry and components for identifying a physical location of the patient 104. For example, the patient worn sensor 102 can include a GPS unit or a radio signal triangulation based location determination device. A GPS unit or other location determination circuitry included within the patient worn sensor 102 can be used, for example, to identify a location of a patient when the patient is not located where the patient should be at a specified time. The GPS unit can be used to locate patients suffering from dementia or other mental illnesses who are prone to wandering and becoming lost. As another example, if the accelerometer in the patient worn sensor 102 determines that the patient 104 has fallen, the patient worn sensor 102 can transmit an alert to one or more caregivers that includes the location of the patient 104 to allow the caregivers to more easily determine where the patient 104 has fallen and attend to the patient 104's needs quickly and effectively.

Other components that can be included as part of the patient worn sensor 102 include a power supply, buttons or other input mechanisms for receiving user input, one or more audible alarms or speakers, and display lights or a display screen. A power supply for the patient worn sensor 102 can take the form of a battery pack for receiving standard disposable batteries, a rechargeable battery, or a removable battery pack that can be replaced with a fully charged battery pack. The patient worn sensor 102 can further include input mechanisms such as, for example, buttons, keys, or a touch screen. The input mechanisms can allow the patient 104 or a caregiver to adjust settings for the patient worn sensor 102, perform various tests (such as sensor tests, battery power level tests, etc.) or reset one or more alarms for the patient worn sensor 102. The input mechanisms can also allow the patient 104 to place a distress call (e.g., to a caregiver or to a hospital alert system) if the patient 104 is in need of assistance.

The patient worn sensor 102 is configured to communicate with one or more other computing devices, either through wired or wireless communication. For example, the patient worn sensor 102 can use Bluetooth, WiFi, or a cellular communication protocol to communicate with other computing devices such as bedside monitors, personal computers, tablet devices, mobile phones, or central servers. As an example, the patient worn sensor 102 can transmit vital sign information collected from the patient 104 to a tablet device or personal computer functioning as a bedside monitor. The table or personal computer can process received information and display the information in a readably understandable format to one or more caretakers or other users. For example, a tablet device can receive vital sign information from the patient worn sensor 102 through a Bluetooth connection and display an electrocardiogram (ECG) waveform for the patient as well as information on the patient's heart rate, respiration rate, blood oxygenation level, body temperature, and/or other vital signs. As another example, the patient worn sensor 102 can be periodically connected to a computing device (such as a bedside monitor) through a wired connection to allow information collected by the patient worn sensor 102 to be stored, processed, and displayed by the computing device and/or transferred to one or more other computing devices (e.g., personal computers, servers located at the hospital, cloud storage servers, etc.).

Information recorded by the patient worn sensor 102 can be transmitted to other computing devices for use in both real-time or near real-time analysis of the patient 104's condition as well as for tracking of vital sign information for the patient 104 over time. For example, the information recorded by the patient worn sensor 102 can be transmitted to a display device to allow caregivers to observe the information and make adjustments to patient care for the patient 104 based on the information. The information can also be transmitted to a central information repository to allow historical vital sign and other information for the patient to be logged. This can allow caregivers to access the information to identify trends for the patient, assist with diagnosis, track the progress of patient recovery, or potentially identify previously unnoticed issues or anomalies. Caregivers can review the stored vital sign information to identify trends or patterns that can be indicative of issues related to the patient 104's health that may be more difficult to identify based on only real-time or near real-time information. Both real-time and historical vital sign and other information for a patient can be accessed by caregivers who are not at the same physical location as the patient. This can allow for increased monitoring of patients while allowing doctors and other caregivers to observe and care for a larger number of patients spread across various different locations. For example, vital sign information collected by the patient worn sensor 102 can be transmitted to a mobile device owned by the patient 104 (e.g., a smart phone) to allow the patient 104 to view the information. The information can further be transmitted to a central server that can be accessed by one or more caregivers (e.g., using personal computers or mobile devices) to allow the caregivers to view the collected information and make patient care decisions for the patient 104 from a location that is remote from where the patient 104 is located.

Figure 2A:
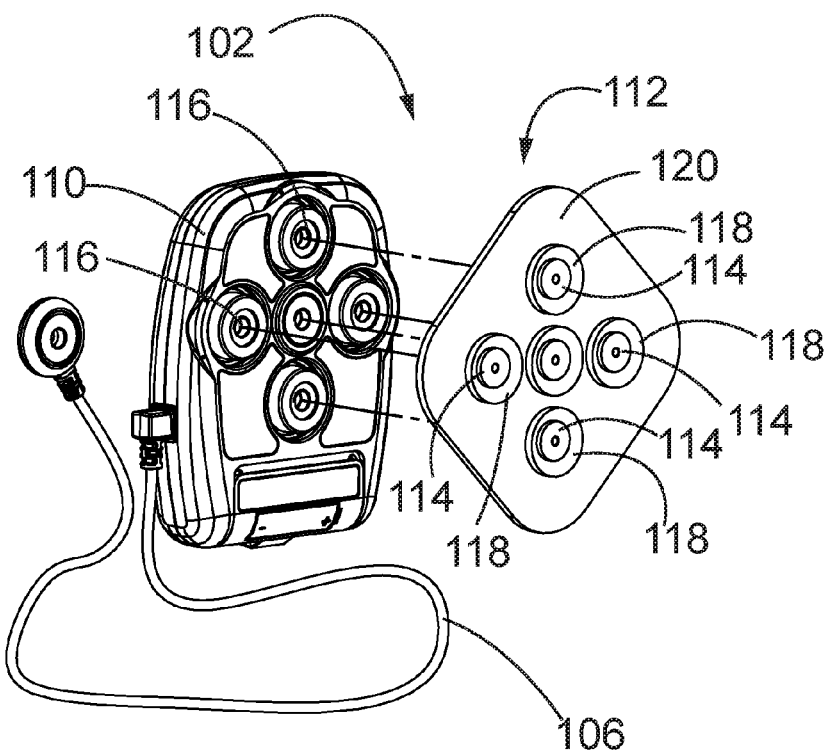
FIGS. 2A-2B show perspective views of an electrode pad assembly detached from and positioned relative to a sensor housing assembly of a patient worn sensor.
Figure 2B:
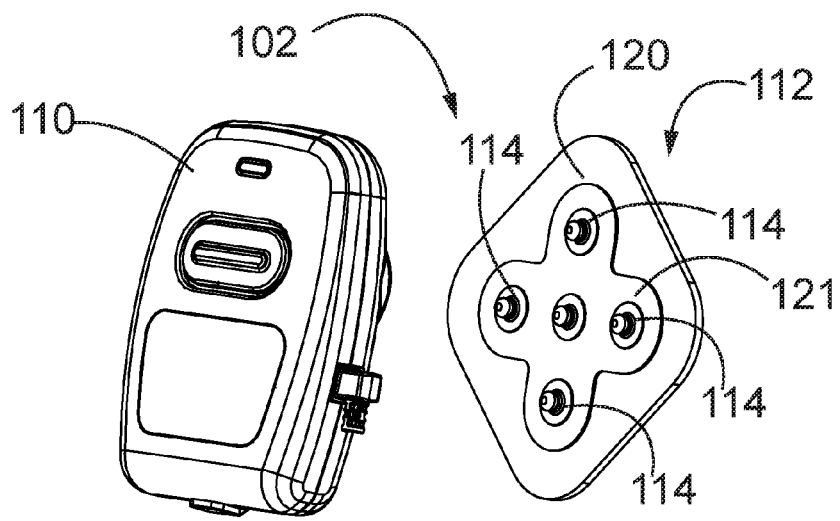

FIGS. 2A and 2B show a sensor housing 110 of the patient worn sensor 102 positioned relative to an electrode pad assembly 112 of the patient worn sensor 102. The sensor housing 110 can include electrical components for processing signals received from and detected in association with the patient and for transmitting the information to other computing devices. In some implementations, the electrode pad 112 can be configured to be disposable such that the electrode pad 112 can be removed from the sensor housing 110 and replaced by another electrode pad having an identical or similar design to that of the electrode pad 112. As described above, the electrode pad 112 includes electrodes 114 that are configured to engage electrical contacts 116 of the sensor housing 110. Each electrode 114 can include a hydrogel layer 118 for contacting the skin of a patient and collecting vital sign information. The electrodes 114 can convey signals from the patient through the electrical contacts 116 to the components within sensor housing 110 for processing by the patient worn sensor 102 and/or transmission to other computing devices.

The electrode pad 112 includes an elastic layer 120 coated with an adhesive coating for contacting and adhering to the skin of a patient. The elastic layer can be, for example, a foam layer (e.g., foamed polyethylene) or a layer of another suitably flexible and elastic material. The elastic layer 120 can allow for a degree of flexibility as the patient moves. This can allow the electrodes 114 to remain in contact with the patient as the patient moves by allowing the electrodes 114 a degree of freedom of motion relative to each other.

In some embodiments, the electrode pad 112 further includes a stabilizing sheet 121 positioned parallel to and affixed to the elastic layer 120. The electrodes 114 extend through both the elastic layer 120 and the stabilizing sheet 121. As shown in FIG. 2B, in some embodiments the surface area of the stabilizing sheet 121 is less than the surface area of the elastic layer 120. The stabilizing sheet 121 provides additional structural integrity for the electrode pad assembly 112 by restricting movement of the electrodes 114 relative to each other along the X-axis and Y-axis directions (e.g., directions parallel to the primary surfaces of the elastic layer 120 and the stabilizing sheet 121) while allowing for some degree of movement of the electrodes 114 relative to each other in the Z-axis direction. For example, the elastic layer 120 may allow for a degree of stretching in the X and Y directions, the stabilizing sheet 121 can restrict the elastic layer 120 from stretching in the X and Y directions. Such reduction in movement in the X and Y directions can reduce signal noise and increase signal quality for vital sign signals collected from a patient to which the electrode pad assembly 112 is affixed by reducing unwanted changes in voltage caused by shifting of the electrodes relative to each other.

Additionally, as described above, the patient worn sensor 102 includes the temperature sensor 106 that extends from the sensor housing 110 of the patient worn sensor 102 to allow one or more electrodes positioned at a distal end of the temperature sensor 106 to be positioned under a patient's armpit, on the underside of the patient's arm, or on the side of the patient's torso to record skin temperature information for the patient. The one or more electrodes of the temperature sensor 106 can, as described above for the electrodes 114 of the electrode pad 112, include hydrogel layers for contacting the skin of a patient and collecting vital sign information including temperature information.

Figure 3A:
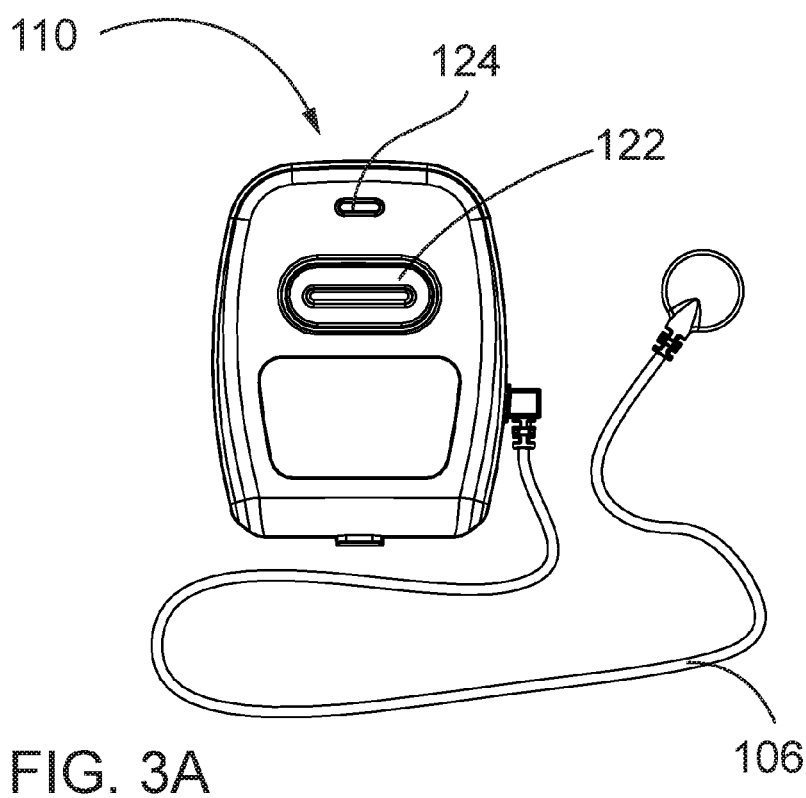
FIGS. 3A-3B show top and bottom views of a sensor housing assembly of a patient worn sensor.

FIG. 3A shows a top view of the sensor housing 110 of the patient worn sensor 102. The sensor housing 110 includes one or more control buttons 122 positioned on the top side of the sensor housing 110 (e.g., the side configured to be positioned away from the patient when the patient worn sensor 102 is attached to a patient's chest). The control button 122 can be used to receive user input and control settings and functions of the patient worn sensor 102. For example, the control button 122 can be used to perform tests various tests such as sensor tests, battery power level tests, audible alarm tests, light tests, etc. As another example, the control button 122 can be used to stop a flashing light of the patient worn sensor 102 or stop an audible alarm (or change the volume of an audible alarm) of the patient worn sensor 102. Other functions of the control button 122 can include initiating a patient distress alert, initiating communication with another device, or logging a patient event or symptom.

In some implementations, the sensor housing 110 can also include display lights, a display screen, or other display mechanisms. For example, one or more LED lights 124 can indicate a current status of one or more vital signs of a patient wearing the patient worn sensor 102 or a current status of one or more components of the patient worn sensor 102. For example, the LED light 124 can indicate that a battery of the patient worn sensor 102 is low, while another LED can indicate that a communications unit (e.g., wireless Bluetooth communication circuitry) is malfunctioning. In some implementations, the LED light 124 can illuminate in a variety of colors or flash at varying rates to convey information. In some implementations, the sensor housing 110 can include a display screen to provide indications of settings of the patient worn sensor 102 or vital sign information or other information collected by the patient worn sensor 102. For example, a display screen can show one or more ECG readings for a patient.

Figure 3B:
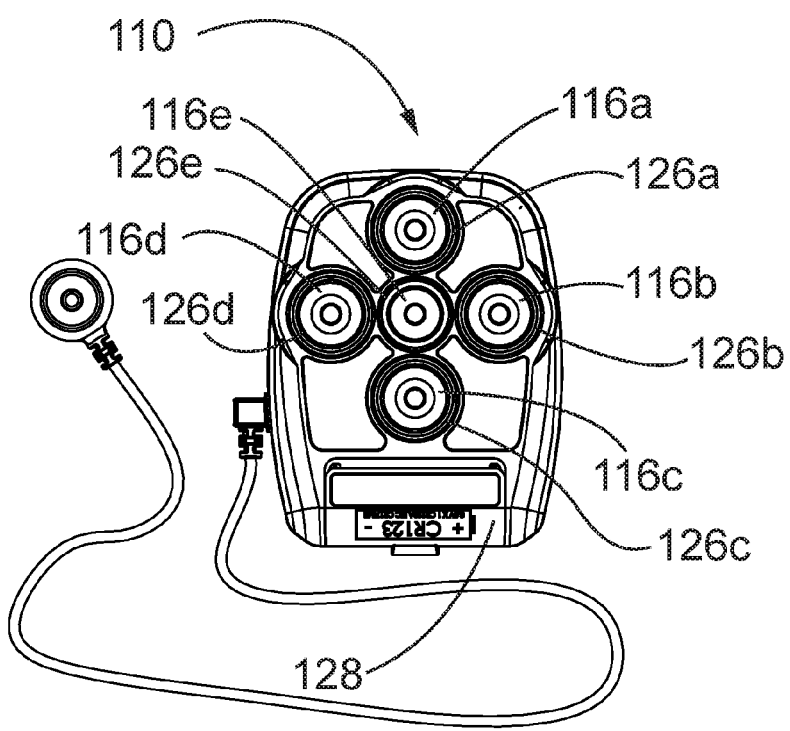

FIG. 3B shows a top view of the sensor housing 110 of the patient worn sensor 102. As shown in this example, the sensor housing 110 includes a battery compartment 128 for storing one or more batteries or battery packs for the patient worn sensor 102. The battery compartment 128 can be accessed using a battery compartment door to allow the one or more batteries or battery packs of the patient worn sensor 102 to be readily removed and replaced.

The example shown in FIG. 3B also shows a more detailed view of the electrical contacts 116 of the sensor housing 110. As described above with respect to FIGS. 2A-B, the electrical contacts 116 are configured to engage electrodes of an adhesive electrode pad to receive signals collected from a patient. The signals are relayed to electrical components housed within the sensor housing 110 for processing and/or transmission to other computing devices. In the example shown, the electrical contacts 116 include snap connectors for engaging corresponding electrodes of an adhesive electrode pad. In the example shown, the electrical contacts 116 are arranged in a clover pattern with the electrical contact 116e in a substantially central location and the electrical contacts 116a-d spaced equidistantly around the electrical contact 116e. In this configuration, the electrical contact 116e is positioned substantially at the center of the other electrical contacts 116, but is positioned off center from the bottom surface of the sensor housing 110. In other configurations, the sensor housing 110 can include more or less electrical contacts 116 than shown in FIG. 3B. For example, the sensor housing 110 can include a center electrical contact surrounded by six other electrical contacts.

The sensor housing 110 of the patient worn sensor 102 includes stabilizing boots 126 extending from the sensor housing 110 to surround each of the electrical contacts 116. Each stabilizing boot 126 encircles a respective electrical contact 116 of the sensor housing 110. The stabilizing boots 126 are configured to contact a surface of an adhesive electrode pad affixed to the sensor housing 110 and absorb shock caused by motion of the patient, thereby providing a more stable signal from the electrodes. The stabilizing boots 126 allow the patient to move freely while wearing the patient worn sensor 102 in that the stabilizing boots 126 absorb shock caused by motion of the electrodes of the adhesive electrode pad with respect to each other. The stabilizing boots can also absorb motion caused by flexing of the adhesive electrode pad as the adhesive electrode pad moves with the patient's skin. The stabilizing boots are further configured to absorb shock due to motion caused by other movements of the patient, such as walking, running, rolling over, etc.

The stabilizing boots 126 can absorb shock caused by movement of the patient while still allowing for a degree of compliance in the X, Y, and Z directions. In some implementations, the stabilizing boots 126 can provide stability to the connection between the sensor housing 110 and the adhesive electrode pad by providing for a greater degree of movement in a Z-axis direction than in X-axis and Y-axis directions of the sensor housing 110 relative to the patient. The Z-axis can be, for example, a direction that is substantially perpendicular to the patient's skin (and therefore the contact surface of the adhesive electrode pad) while the X-axis and Y-axis directions are substantially parallel to the patient's skin (and therefore the contact surface of the adhesive electrode pad). When in use, an adhesive side of the adhesive electrode pad portion of the patient worn sensor 102 is affixed to a patient while the opposite side of the adhesive electrode pad is attached to the sensor housing 110 by way of snap connectors of electrodes of the adhesive electrode pad engaging the electrical contacts 116. Once the patient worn sensor 102 is attached to the patient, the patient is free to move, which can cause shifting in the relative location of contact points on the patient's skin at which the electrodes of the adhesive electrode pad contact the patient. The stabilizing boots 126 can absorb some or all of the motion caused by movement of the patient, thereby reducing negative effects on signal quality of signals received by the electrodes of the adhesive electrode pad. In some implementations, the stabilizing boots 126 extend beyond the electrical contacts 116 to at least partially encircle portions of the electrodes of the adhesive electrode pad.

In some implementations, the stabilizing boots 126 can be formed using an over molding process, such that the stabilizing boots 126 are integrated with a portion of the sensor housing 110 (e.g., a bottom portion of the sensor housing) as an integral piece. The over molding process allows for the stabilizing boots 126 to be made from a material having less rigidity than a material used to form other portions of the sensor housing 110, while still allowing the stabilizing boots 126 to be formed as an integral piece with at least a portion of the sensor housing 110.

In some implementations, the stabilizing boots 126 are formed from a thermoplastic elastomer (TPE) material. For example, the stabilizing boots can be formed from a 70 Shore A TPE material using an over molding process. In some embodiments, the stabilizing boots 126 have a hardness of between about 50 and about 90 on the Shore A scale. In some embodiments, the stabilizing boots 126 have a hardness of between about 60 and about 80 on the Shore A scale. In some embodiments, the stabilizing boots 126 have a hardness of between about 65 and about 75 on the Shore A scale. In some embodiments, the stabilizing boots 126 have a hardness of about 70 on the Shore A scale.

In some embodiments, the stabilizing boots 126 have a height (i.e., in the direction that is perpendicular to the plane of the bottom surface of the sensor housing shown in FIG. 3B that is intended to face a body of a patient) of between about 3 mm and about 7 mm. In some embodiments, the stabilizing boots 126 have a height of between about 4 mm and about 6 mm. In some embodiments, the stabilizing boots 126 have a height of about 5.25 mm. In some embodiments, the stabilizing boots 126 have an outer circumference of between about 13 mm and about 16 mm. In some embodiments, the stabilizing boots 126 have an outer circumference of between about 14 mm and about 15 mm. In some embodiments, the stabilizing boots 126 have an outer circumference of about 14.2 mm.

In some implementations, the stabilizing boots 126 can allow for a degree of freedom in the movement of the sensor housing 110 relative to the patient in the Z-axis direction that is greater than the amount of movement allowed in lateral (X and Y) directions. This can be achieved, for example, by using a material for the stabilizing boots 126 that is more rigid in the X and Y directions than in the Z direction. Such reduction in movement in the X and Y directions can reduce signal noise and increase signal quality for vital sign signals collected from the patient by reducing unwanted changes in voltage caused by shifting of the components of the patient worn sensor 102 relative to the patient. This can also reduce the need for applying filtering techniques for filtering out signal noise that occurs due to movement of the patient and movement of the patient worn sensor 102 relative to the patient.

In some implementations, one or more of the electrical contacts 116 serves as a drive electrical contact (providing electrical current) and a second electrode serves as an extraction electrode for receiving the electrical current while the other electrical contacts 116 are detecting electrical contacts for detecting changes in electrical signals within the patient's body. For example, the electrical contact 116e can be a drive electrical contact for providing an electrical current to a patient to which the patient worn sensor 102 is affixed while the electrical contact 116c serves as an extraction electrode and the remaining electrodes serve as sensing electrodes.

In some implementations, the stabilizing boot 126 surrounding the drive electrical contact can be more rigid than the stabilizing boots 126 surrounding the other electrical contacts, thereby restricting the movement of the drive electrical contact with respect to the patient more than the movement of the other electrical contacts 116. For example, if the electrical contact 116e is the drive electrical contact, then the stabilizing boot 126e that encircles the electrical contact 116e can be more rigid than the other stabilizing boots 126a-d. In some implementations, the stabilizing boot 126e is only more rigid than the stabilizing boots 126a-d in the Z-direction, while in other implementations, the stabilizing boot 126e is more rigid than the stabilizing boots 126a-d in all directions. In some implementations, it is beneficial to have the drive electrical contact (and therefore, the more rigid stabilizing boot) positioned in a relatively central location relative to the other electrical contact/stabilizing boot pairs. For example, the electrical contact 116e can be the drive electrical contact while the stabilizing boot 126e is more rigid than the other stabilizing boots 126a-d since the electrical contact 116e and the stabilizing boot 126e are in a relatively central position with respect to the other electrical contact 116/stabilizing boot 126 pairs. A central location for the more rigid stabilizing boot 126e can allow for a greater effect of the motion reduction and stabilizing properties of the stabilizing boot 126e.

Placement of the more rigid stabilizing boot around a drive electrical contact of the electrical contacts 116 allows the more rigid stabilizing boot to serve as an anchor point for the sensor housing 110 without affecting the sensing ability of the patient worn sensor 102 since the drive electrical contact does not perform sensing functions, but merely serves as a source of electrical current. In essence, the other, less rigid stabilizing boots 126 are allowed to flex with respect to the more rigid stabilizing boot (serving as an anchor) while absorbing shock caused by motion of the patient. This allows the other, non-drive electrical contacts 116 a greater degree of motion.

In some embodiments, fewer than all of the electrical contacts 116 are surrounded by a stabilizing boot. For example, the electrical contacts 116b, 116d, and 116e may be encircled by stabilizing boots 126b, 126d, and 126e respectively while the electrical contacts 116a, and 116c are not surrounded by stabilizing boots.

Figure 4:
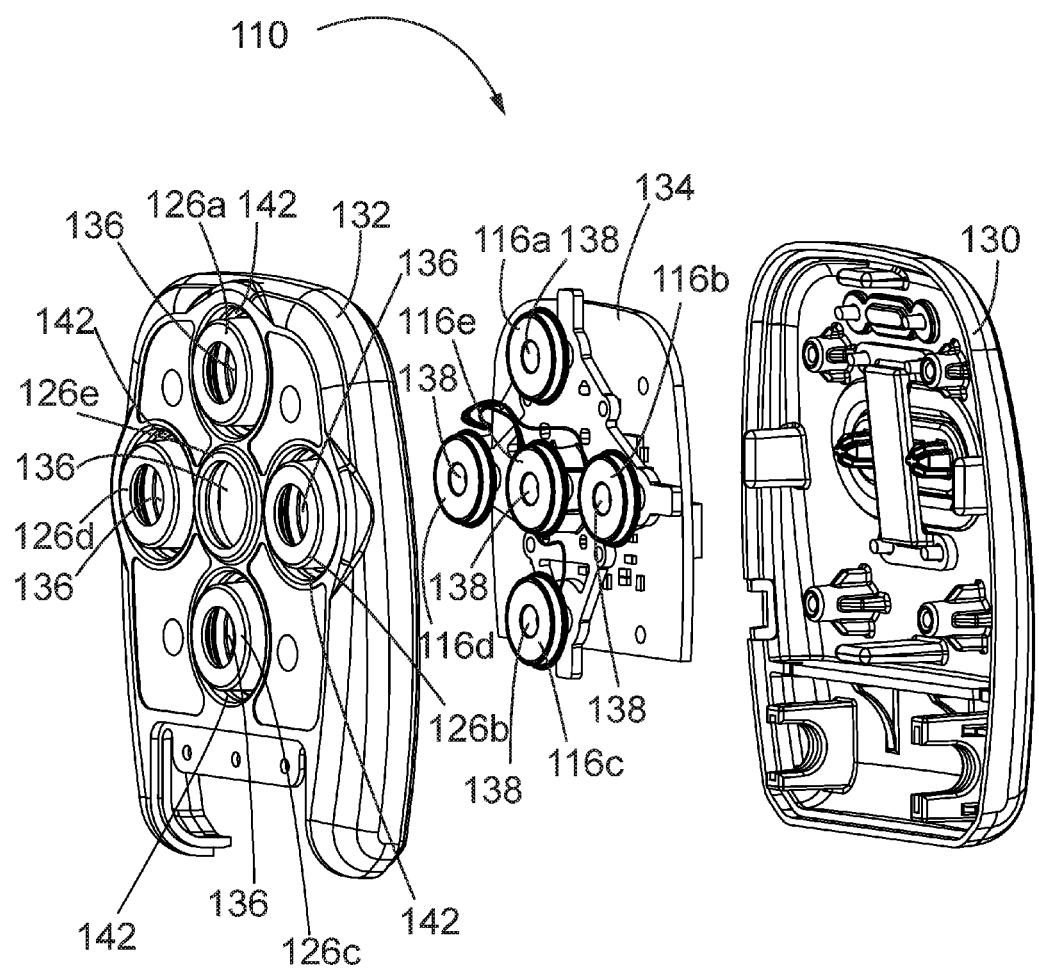
FIG. 4 shows an exploded view of components of the sensor housing assembly of FIGS. 3A-3B.

FIG. 4 shows an exploded view of components of the sensor housing assembly 110 of FIGS. 3A-3B with the battery door of the battery compartment 128 and the battery or battery pack removed. As described above, the sensor housing 110 can be part of a patient worn sensor 102 (such as a chest sensor) that is configured to engage an adhesive electrode pad. The sensor housing 110 includes a top outer case portion 130. The top outer case portion 130 can be configured to engage a bottom outer case portion 132 of the sensor housing 110 to encase and protect other components of the sensor housing 110. The top outer case portion 130 and bottom outer case portion 132 can be made from molded plastic or another material that is suitably light weight so as to facilitate easy attachment to a patient while also structurally strong enough to protect inner components of the sensor housing 110 from damage if the sensor housing 110 is dropped. The top and bottom outer case portions 130 and 132 can, for example, be plastic injection molded parts molded from a high impact plastic such as polycarbonate (PC), acrylonitrile butadiene styrene (ABS) or an ABS/PC blend. The top outer case portion 130 and bottom outer case portion 132 can also be configured to engage each other in a water-tight or semi-water-tight seal to prevent moisture from reaching the inner components of the sensor housing 110. In some implementations, the top outer case portion 130 and/or bottom outer case portion 132 can include one or more buttons for controlling the sensor housing 110 (e.g., changing settings for the sensor housing 110). In some implementations, the top outer case portion 130 and/or bottom outer case portion 132 can include one or more lights (e.g., LEDs) for indicating an alarm state for a patient wearing the sensor housing 110, or a functional problem with the sensor housing 110 (such as loss of communication, or low battery).

The sensor housing 110 includes a circuit board 134 that includes various processing components implemented as integrated chips and other electrical components. The circuit board 134 can include one or more processors for processing signals received from a patient as well as one or more communications modules for communicating with other computing devices using one or more communications protocols (e.g., Bluetooth, WiFi, cellular communication, etc.). Other components that can be included in the circuitry of the circuit board 134 include one or more accelerometers, a GPS or other location detection unit, temperature sensors for sensing environmental temperature, light sensors for sensing environmental light, input modules for receiving user input via controls of the sensor housing 110, and output modules for conveying information to a user through the control of output devices such as lights, speakers, audible alarms, or display screens.

The sensor housing 110 further includes the electrical contacts 116. The electrical contacts 116 can be mounted to the circuit board 134 and aligned with apertures 136 of the bottom outer case portion 132 to allow at least a portion of each of the electrical contacts 116 to be exposed to the outside of the sensor housing 110. Each electrical contact 116 includes a female snap connector 138 for receiving a male snap connector of a corresponding electrode of an adhesive electrode pad connected to the sensor housing 110. The coupling of the male snap connectors of the electrodes to the female snap connectors 138 forms both a mechanical connection and an electrical connection between the adhesive electrode pad and the sensor housing 110. The mechanical coupling of the male snap connectors of the electrodes to the female snap connectors 138 physically connects the adhesive electrode pad to the sensor housing 110 to hold the sensor housing 110 in place with respect to the adhesive electrode pad. Additionally, each connection of a male snap connector of an electrode of the adhesive electrode pad to a female snap connector 138 forms an electrical connection for the transmission of signals from a patient wearing the patient worn sensor 102 to the processing components of the circuit board 134.

The bottom outer case portion 132 further includes the stabilizing boots 126a-e that define each of the apertures 136 and provide stability for the sensor housing 110 when the sensor housing 110 is coupled to an electrode pad assembly and affixed to a patient. Each of the stabilizing boots 126a-e is configured to surround at least a portion of a corresponding electrical contact 116. The stabilizing boots 126a-e of the sensor housing 110 are configured to provide mechanical stability and reduce unwanted signal noise generated due to unwanted motion of the sensor housing 110 and or adhesive electrode pad with respect to a patient that is wearing the patient worn sensor 102. In the example shown, the bottom outer case portion 132 includes grooves 142 that surround each of the stabilizing boots 126a-e. The grooves 142 allow the stabilizing boots 126a-e to move to a degree within the X and Y directions with respect to the bottom outer case portion 132, thereby reducing signal noise due to unwanted motion artifacts. As described above, the stabilizing boots 126a-e are also configured to compact to a degree in the Z direction to allow for compliance in the Z direction.

Figures 5A, 5B:
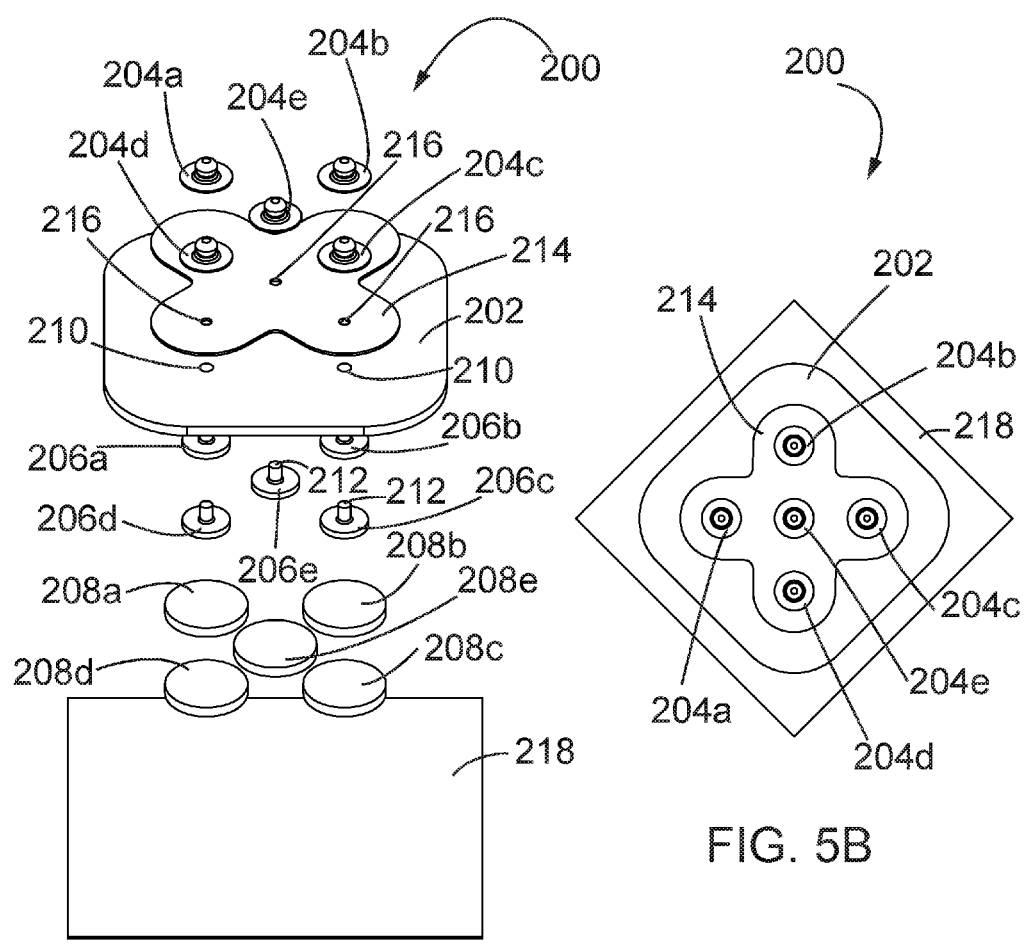
FIG. 5A shows an exploded view of components of an electrode pad assembly.
FIG. 5B shows an assembled view of the electrode pad assembly of FIG. 5A.

FIG. 5A shows an exploded view of components of an electrode pad assembly 200. The electrode pad assembly 200 includes an elastic layer 202 as well as electrodes formed from upper electrode portions 204a-e, lower electrode portions 206a-e, and hydrogels 208a-e. As described above for the elastic layer 120, the elastic layer 202 can be a foam layer (e.g., foamed polyethylene) or a layer of another suitably elastic and flexible material. The elastic layer 202 should allow for a degree of elasticity or stretching in the X and Y directions (parallel to the main surface of the elastic layer 120) as well as a degree of flexibility in the Z direction (perpendicular to the main surface of the elastic layer 120). In some implementations, the elastic layer 202 can be made of several layers of one or more different materials. In some implementations, the elastic layer 202 is made from one or more composite materials. The electrode pad assembly 200 further includes apertures 210 disposed within the elastic layer 202 that define the relative positions of the electrodes with respect to each other. Extending members 212 of each of the lower electrode portions 206a-e extend through the apertures 210 and engage the upper electrode portions 204a-e. The lower electrode portions 206a-e and upper electrode portions 204a-e are held in place with respect to the elastic layer 202 when the lower electrode portions 206a-e engage the upper electrode portions 204a-e in an assembled state (as shown in FIG. 5B). The lower electrode portions 206a-e and the upper electrode portions 204a-e can be manufactured from metal or one or more other conductive materials to provide for electrical connectivity between the lower electrode portions 206a-e and the upper electrode portions 204a-e when the electrode pad assembly 200 is in an assembled state. For example, the lower electrode portions 206a-e and the upper electrode portions 204a-e can be manufactured from silver, silver chloride, or a combination of the two materials.

The upper electrode portions 204a-e additionally include male connectors for engaging and providing electrical connectivity to corresponding female connectors of a sensor housing. For example, the male connectors of the upper electrode portions 204a-e can be male snap connectors configured to engage the female snap connectors 138 of the electrical contacts 116 of the sensor housing 110 shown in FIG. 4.

When the electrode pad assembly 200 is in an assembled state (as shown in FIG. 5B) the hydrogels 208a-e are affixed to bottom surfaces of the lower electrode portions 206a-e. The hydrogels 208a-e are configured to contact the skin of a patient and provide electrical connectivity between the skin of the patient and the lower electrode portions 206a-e to convey signals from the skin of the patient to the lower electrode portions 206a-e (and ultimately electrical contacts of a sensor housing). The hydrogels 208a-e can be any suitable biocompatible gel such as, for example, Amgel AG603 hydrogels.

The electrode pad assembly 200 further includes a stabilizing sheet 214 positioned parallel to and affixed to the elastic layer 202 when the electrode pad assembly 200 is in an assembled state (as shown in FIG. 5B). The stabilizing sheet 214 includes apertures 216 positioned to correspond to and align with the apertures 210 of the elastic layer 202 when in an assembled state. When assembled, the extending members 212 of the lower electrode portions 206a-e extend through the apertures 210 and through the apertures 216 to engage the upper electrode portions 204a-e. The stabilizing sheet 214 provides additional structural integrity for the electrode pad assembly 200 by restricting movement of the electrodes relative to each other along the X-axis and Y-axis directions (e.g., directions parallel to the primary surfaces of the elastic layer 202 and the stabilizing sheet 214) while allowing for some degree of movement of the electrodes relative to each other in the Z-axis direction. Such reduction in movement in the X and Y directions can reduce signal noise and increase signal quality for vital sign signals collected from a patient to which the electrode pad assembly 200 is affixed by reducing unwanted changes in voltage caused by shifting of the electrodes relative to each other.

In some embodiments, the stabilizing sheet 214 is formed from a single sheet of material that engages each of the electrodes of the electrode pad assembly 200. The stabilizing sheet 214 can be, for example, label stock that is suitable for use in medical settings and that is sufficiently rigid so as to restrict movement of the electrodes in the X and Y directions while allowing for a greater degree of movement of the electrodes in the Z direction. When in an assembled state, the stabilizing sheet 214 can be secured to the elastic layer 202 by an adhesive. For example, the stabilizing sheet 214 can include an adhesive layer for bonding to the elastic layer 202.

The elastic layer 202 can be formed from a foam material or other suitably elastic material that allows for a degree of stretching or movement in the X and Y directions. For example, in situations in which the stabilizing sheet 214 is not present, the elastic layer 202 can be formed from a material that allows for stretching in the X and Y directions, and therefore allows for a degree of displacement of the electrodes relative to each other in the X and Y directions. The stabilizing sheet 214 can be included in the electrode pad assembly 200 to reduce the degree of motion of the electrodes in the X and Y directions relative to each other by preventing the elastic layer 202 from being stretched in the X and Y directions or by limiting the stretching of the elastic layer 202 in the X and Y directions. For example, the stabilizing sheet 214 allows for a degree of stretching in the X and Y directions that is less than the degree of stretching in the X and Y directions allowed by the elastic layer 202. As another example, the stabilizing sheet 214 allows for substantially zero stretching in the X and Y directions. In some embodiments, the stabilizing sheet 214 is formed from a relatively flexible material that allows for movement of the electrodes relative to each other in the Z direction while restricting movement of the electrodes in the X and Y directions.

By limiting the degree of displacement of the electrodes with respect to each other, the stabilizing sheet 214 can reduce baseline wander of a signal trace (such as a visual display of an ECG signal) being viewed by a clinician. The stability provided by the stabilizing sheet 214 reduces the motion artifact of the ECG signal and other signals collected by a sensor assembly that includes the electrode pad assembly 200.

In the example shown, the stabilizing sheet 214 includes five apertures 216, each of the apertures 216 configured to receive one of the extending members 212 of the lower electrode portions 206a-e. In the example shown, the apertures 216 (and the apertures 210) are positioned such that when the electrode pad assembly 200 is assembled, the electrodes are positioned with one electrode in the center and four electrodes spaced substantially equidistantly around the electrodes.

In the example shown, the stabilizing sheet 214 has a clover-like shape (i.e., a four leafed clover shape, or rounded plus-sign shape) that engages less than the entire upper surface of the elastic layer 202. This allows for the stabilizing sheet 214 to efficiently engage each of the electrodes and provide enough material surrounding each of the electrodes to provide the required additional stability, while allowing for greater flexibility of the elastic layer 202 in areas not covered by the clover shaped stabilizing sheet 214. In some other embodiments, the stabilizing sheet 214 can have a square or rectangular shape or a substantially square or rectangular shape with rounded corners. In some other embodiments, the stabilizing sheet 214 can have the same or substantially the same X and Y dimensions as the elastic layer 202 such that when the stabilizing sheet 214 engages the elastic layer 202, the stabilizing sheet 214 completely or substantially completely covers an entire upper surface of the elastic layer 202.

In some other embodiments, the stabilizing sheet 214 can have a different shape for engaging a different number of electrodes. For example, the electrode pad assembly 200 can include seven electrodes, with one electrode positioned at the center and the other six electrodes spaced substantially equidistantly around the center electrode. In such a configuration, the stabilizing sheet 214 can take the form of a six pointed star having rounded points (i.e., a six leafed clover shape).

In some embodiments, the elastic layer 202 includes an adhesive layer covering at least a portion of the bottom surface of the elastic layer 202. The adhesive layer is configured to engage the skin of a patient and affix the electrode pad assembly 200 to the patient's skin such that the hydrogels 208a-e are in contact with the patient's skin for collecting vital sign signals from the patient. In some embodiments, the electrode pad assembly 200 is affixed to a backing layer 218 for covering the hydrogels 208a-e and the bottom surface of the elastic layer 202 to prevent the adhesive layer of the elastic layer 202 from being exposed prior to use. When in use, the backing layer 218 is removed from the electrode pad assembly 200 and discarded so that the electrode pad assembly 200 can be affixed to the skin of a patient. In some implementations, the backing layer 218 is not part of the electrode pad assembly 200.

Figure 6:
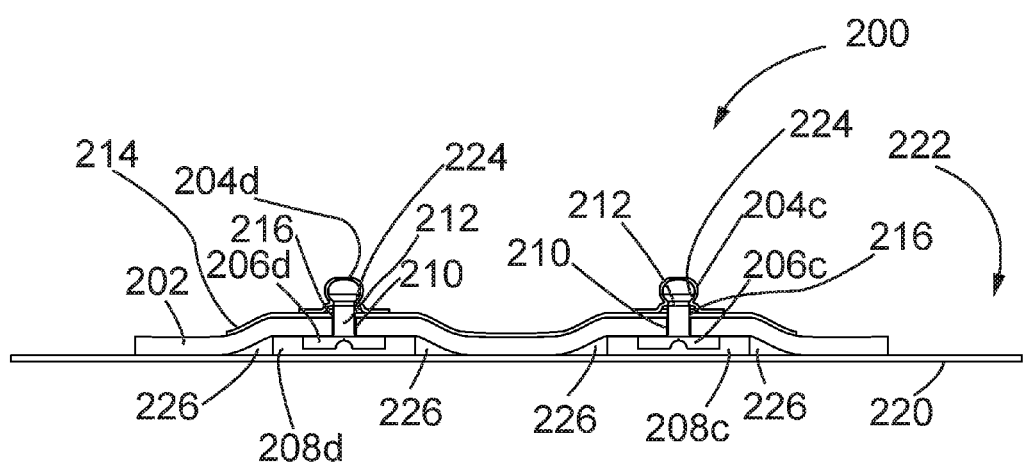
FIG. 6 shows a cross-section view of the electrode pad assembly of FIG. 5B.

FIG. 6 shows a cross-sectional view of the electrode pad assembly 200 affixed to the skin 220 of a patient 222. In the example shown in FIG. 6, the backing layer 218 has been removed from the electrode pad assembly 200 to expose an adhesive layer of the elastic layer 202 to allow the electrode pad assembly 200 to be affixed to the patient 222. FIG. 6 shows the electrode pad assembly 200 in an assembled state and the relative positioning of the electrode components when the electrode pad assembly 200 is assembled. The hydrogels 208 are affixed to bottom surfaces of the lower electrode portions 206. The extending members 212 of the lower electrode portions 206 extend through the apertures 210 of the elastic layer 202 and through the apertures 216 of the stabilizing sheet 214 to engage corresponding female receiving portions 224 of the upper electrode portions 204. The lower electrode portions 206 engage the upper electrode portions 204 to hold the electrodes in place with respect to the elastic layer 202 and to form an electrical connection for conveying electrical signals from the patient 222's skin 220. The cross-sectional view shown in FIG. 6 shows two electrodes of the electrode pad assembly 200, but it should be understood that each electrode of the electrode pad assembly 200 can have a similar configuration to those shown in FIG. 6.

When in place as shown in FIG. 6, the placement of the electrodes and the elastic layer 202 with respect to the patient 222's skin 220 creates a tented structure at the electrode contact points, forming air pockets 226. In some embodiments, the air pockets 226 at least partially encircle the hydrogels 208. In some embodiments, the air pockets 226 completely encircle the hydrogels 208. The air pockets 226 are at least partially defined by the lower surface of the elastic layer 202, edges of the hydrogels 208 and the patient 222's skin 220. The peak height of each air pocket 226 is defined by the height of each respective hydrogel 208 and, in some embodiments, a portion of the respective lower electrode portion 206. In some embodiments, the maximum height of each air pocket 226 is between approximately 0.4 mm and 1.2 mm. In some embodiments, the maximum height of each air pocket 226 is between approximately 0.5 mm and 1.0 mm. In some embodiments, the maximum height of each air pocket 226 is approximately 0.7 mm.

The width of each air pocket 226 is defined by the edges of the respective hydrogel 208 and locations on the patient 222's skin 220 where the elastic layer 202 makes contact with the skin 220. In other words, the width of a particular air pocket 226 is measured from the edge of the respective hydrogel 208 to adhesive contact between the skin 220 and the elastic layer 202. In some embodiments, the width of each air pocket 226 is between approximately 1 mm and 5 mm. In some embodiments, the width of each air pocket is between approximately 2 mm and 4 mm. In some embodiments, the width of each air pocket is approximately 3 mm.

As mentioned above, the cross-sectional view of FIG. 6 shows air pockets 226 formed around two electrodes of the electrode pad assembly, but it should be understood that each electrode of the electrode pad assembly 200 can form a similar air pocket with respect to the elastic layer 202 and the patient 222's skin 220. When in place on the patient 222, the air pockets 226 can help increase stability of the contact between the electrode pad assembly 200 and the patient 222's skin 220 as well as increase the longevity of the connection between the electrode pad assembly 200 and skin 220 over other electrode pads that do not include the air pockets 226.

For example, the air pockets 226 can serve as collection points for collecting and/or trapping air bubbles formed between the elastic layer 202 and the skin 220. In some situations, when the electrode pad assembly 200 is placed on the skin 220, air can become trapped between the elastic layer 202 and the skin 220 and form air bubbles. Such air bubbles can reduce the amount of the elastic layer 202 that is in direct contact with the skin 220 of the patient 222, which can lead to the electrode pad assembly 200 being less securely affixed to the skin 220. The air pockets 226 can serve as collection points for the air bubbles, thereby reducing or eliminating air bubbles that occur between the elastic layer 202 and the skin 220.

The air pockets 226 can also prevent air bubbles from propagating from the elastic layer 202 to the hydrogels 208. Since the air pockets 226 encircle the hydrogels 208, air bubbles trapped between the elastic layer 202 and the skin 220 can move to and be collected by the air pockets 226 and prevented from reaching the hydrogels 208. This prevents air bubbles from forming between the hydrogels 208 and the skin 220. Additionally, any air bubbles that form between the hydrogels 208 and the skin 220 when the electrode pad assembly 200 is affixed to the patient 222 can be collected by the air pockets 226. Reducing and/or eliminating air bubbles between the hydrogels 208 and the skin 220 increases the amount of direct contact between the hydrogels 208 and the skin 220, which leads to an increase in signal quality and reduces distortions or signal noise in signals collected from the patient 222. This can lead to an increased quality in vital sign information collected for the patient 222 by a sensor assembly that includes the electrode pad assembly 200.

In some implementations, the air pockets 226 can also serve as collection points for collecting sweat of the patient 222 or other moisture. In some instances, it is desirable for the electrode pad assembly 200 to be affixed to the patient 222 for an extended period of time. For example, it may be desirable to record and track vital signs for the patient 222 over an extended period of time to monitor a health state of the patient 222 or to diagnose one or more symptoms being experienced by the patient. During such extended use, the patient 222 may sweat. The sweat may affect the bond between the elastic layer 202 and the skin 220 by, for example, reducing adhesive properties of an adhesive layer of the elastic layer 202. The air pockets 226 can serve as collection points that allow the sweat and other moisture present on the skin 220 to accumulate away from the areas where the elastic layer 202 directly contacts the skin 220, thus reducing the negative effects of the sweat on the bond between the elastic layer 202 and the skin 220. In addition to collecting air bubbles and sweat from the patient 222, the air pockets 226 can serve as collection points for collecting any other foreign or undesirable material that may become lodged between the elastic layer 202 and the skin 220 or between the hydrogels 208 and the skin 220.

In some alternative embodiments (not shown) the electrode pad assembly 200 forms additional air pockets that are defined by the lower electrode portions 206, the hydrogels 208, and the elastic layer 202. The additional air pockets can, for example, be positioned above the hydrogels 208 and can completely or partially encircle at least a portion of each of the lower electrode portions 206. These additional air pockets can serve as additional areas for collecting air bubbles trapped between the elastic layer 202 and the skin 220, air bubbles trapped between the hydrogels 208 and the skin 220, and sweat or other moisture from the patient 222 thereby providing the benefits described above with respect to the air pockets 226.

Figure 7:
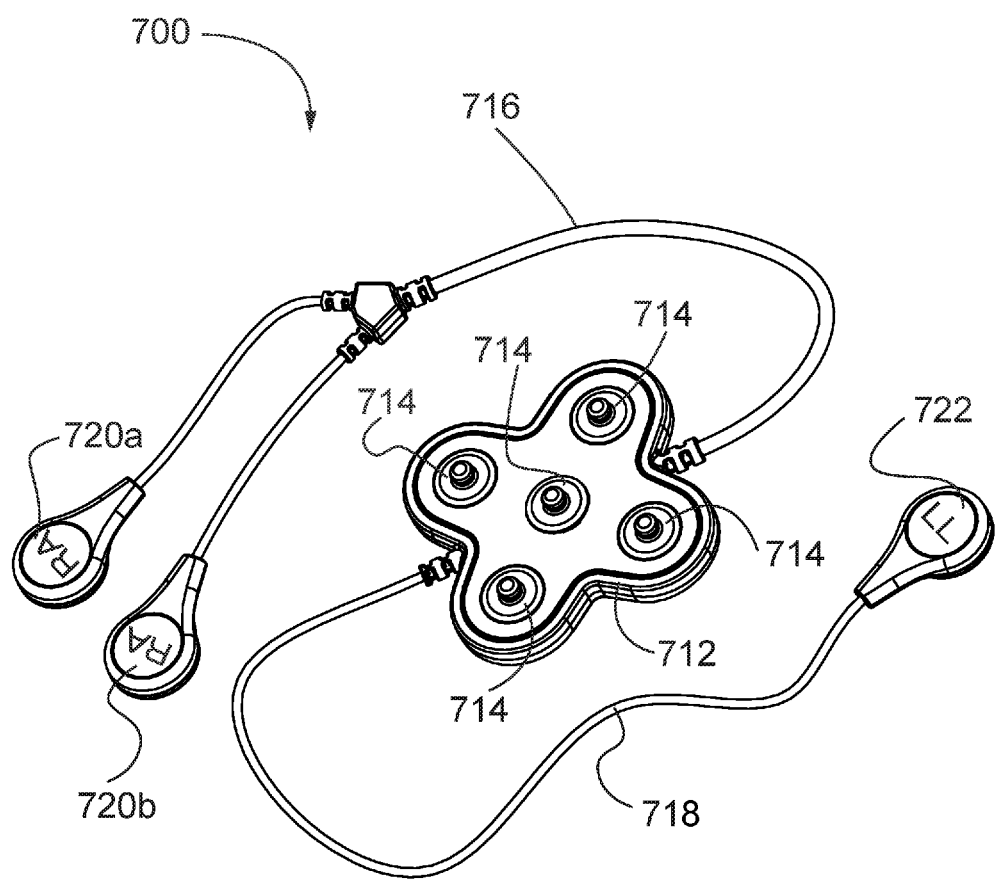
FIG. 7 shows perspective view of an alternative embodiment for an electrode pad assembly.

FIG. 7 shows a perspective view of an electrode assembly 700. The electrode assembly 700 can form a portion of an alternative embodiment of the patient worn sensor 102 described with respect to FIGS. 1, 2A, and 2B. For example, the electrode assembly can be configured to operatively connect to the sensor housing 110 of the patient worn sensor 102 in place of the electrode pad assembly 112. For example, male electrical contacts 714 of the electrode assembly 700 can be configured to operatively connect to the electrical contacts 116 of the sensor housing 110 (shown in FIG. 2A). In some implementations, the electrode assembly 700 can be configured to be disposable such that the electrode assembly 700 can be removed from a sensor housing (such as, for example, the sensor housing 110 shown in FIGS. 2A-B) and replaced by another electrode assembly having an identical or similar design to that of the electrode assembly 700, or replaced by an electrode assembly having a different design than the electrode assembly 700, such as the electrode pad assembly 112. In some implementations, the electrode assembly 700 is reusable and is configured to operatively connect with one or more disposable electrode pads that are configured to affix to a patient's skin.

The electrode assembly 700 includes a main body 712 that includes the electrical contacts 714 and holds the electrical contacts 714 in fixed positions with respect to each other. In the example shown in FIG. 7, the electrical contacts are arranged in a "clover" pattern that corresponds to the clover pattern of the electrical contacts 116 of the sensor housing 110 (as shown in FIG. 3B). Other configurations for the relative positions of the electrical contacts 714 are possible. It is also possible for the electrode assembly 700 to include more or less electrical contacts 714 than shown in the example in FIG. 7. The main body 712 can be formed from a ridged material molded plastic or another material that is suitably light weight so as to facilitate easy attachment to a patient while also structurally strong enough to protect inner components of the main body 712 from damage if the electrode assembly 700 is dropped.

In some implementations, a bottom side of the main body 712 (i.e., the opposite surface of that shown in FIG. 7) can include one or more adhesive layers for affixing to the skin of a patient. For example, the main body 712 of the electrode assembly 700 can be positioned on a patient's chest to monitor vital signs for the patient such as heart rate, respiration rate, etc. Specifically, in some examples, the main body 712 can be affixed on a patient's left pectoral area near the patient's heart.

In some implementations, the main body 712 can include two electrode connections on the bottom surface which are configured to operatively connect with single electrode pads, (for example, standard "red dot" ECG electrodes). For example, the main body 712 can include two electrode connections on the bottom surface for operatively connecting to two single electrode pads. The single electrode pads can include electrodes (including hydrogels) for contacting a patient's skin and collecting vital sign information from the patient. The single electrode pads can also include adhesive layers for affixing the main body 712 to a patient's skin.

The electrode assembly 700 further includes electrode leads 716 and 718. For example, the electrode lead 716 can be a right arm electrode lead and the electrode lead 718 can be a left leg electrode lead. The electrode lead 716 includes two electrode connectors 720a and 720b. The electrode connectors 720a-b can be configured to operatively connect with electrode pads. For example, each of the electrode connectors 720a-b can operatively connect with single electrode pads (for example, "red dot" ECG electrodes) that include electrodes having hydrogels for contacting a patient's skin and collecting vital signs and adhesive layers for securely affixing to the patient's skin. In some implementations, the two electrode connectors 720a-b are positioned on the right side of a patient's signs to collect vital sign information. The electrode lead 716 includes electrically conductive material (e.g., one or more wires) that convey electrical signals from the electrode connectors 720a-b to the main body 712 (and eventually to a sensor housing, such as the sensor housing 110 of FIGS. 2-4).

The electrode lead 718 terminates in an electrode connector 722. Similar to the electrode connectors 720a-b, the electrode connector 722 can be operatively connected to a single electrode pad to collect vital signs from a patient. The electrode lead 718 includes electrically conductive material (e.g., one or more wires) that convey electrical signals from the electrode connector 722 to the main body 712 (and eventually to a sensor housing, such as the sensor housing 110 of FIGS. 2-4). In some implementations, one or more of the electrode connectors 720a-b and 722 (and any electrode connectors positioned on the bottom surface of the main body 712) can connect to electrodes positioned on a multi-electrode pad. The electrode assembly 700 be configured to contact electrical leads of a sensor housing (e.g., the sensor housing 110 of FIGS. 1-3) to convey signals from a patient to the electrical components within the sensor housing of the patient worn sensor. For example, signals detected by electrodes in contact with the electrode connectors 720a-b and 722 (and any electrode connectors positioned on the bottom surface of the main body 712) can be conveyed to a sensor housing.

Figure 8:
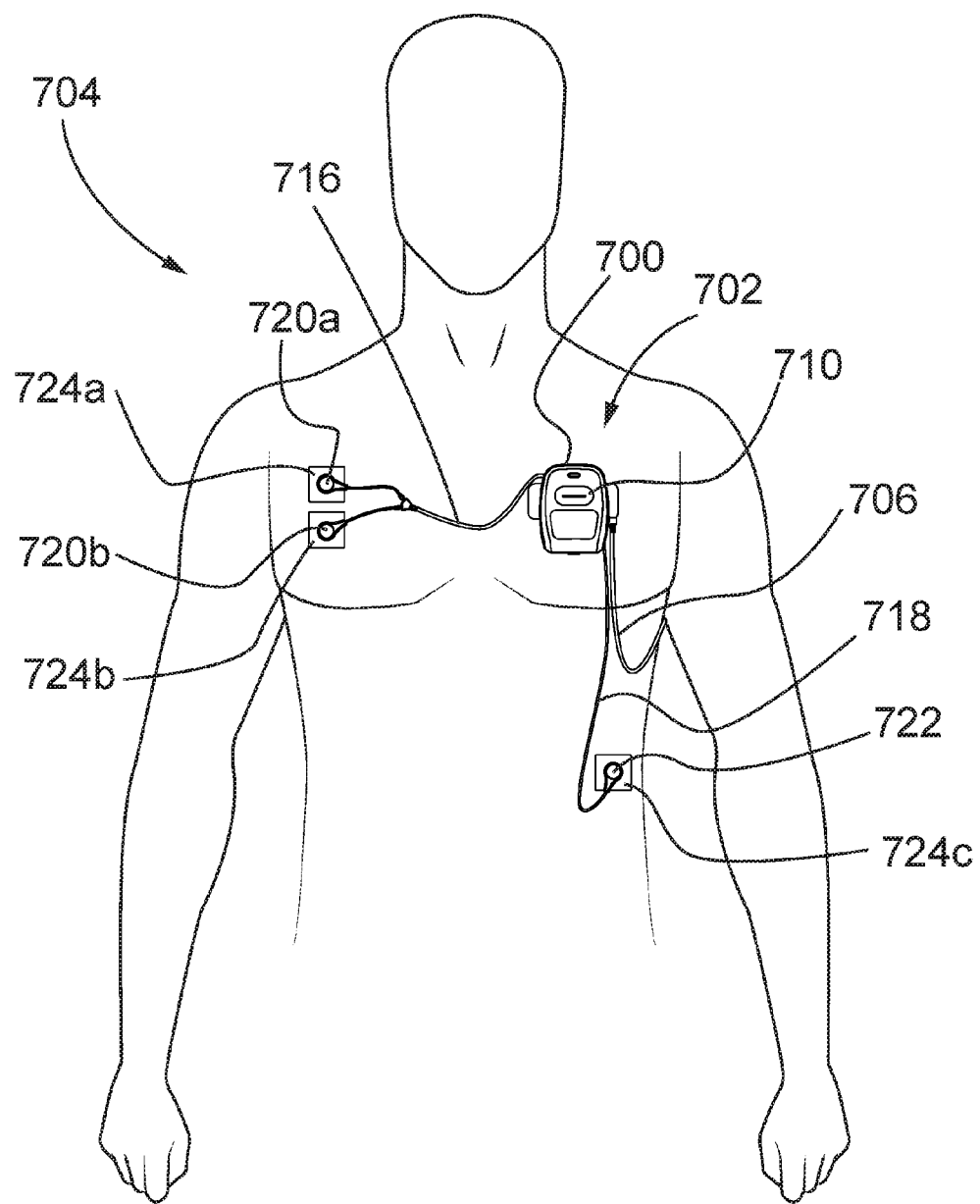
FIG. 8 shows an example patient worn sensor in contact with a patient.

FIG. 8 shows an example patient worn sensor 702 that includes the electrode assembly 700 of FIG. 7. The patient worn sensor 702 is shown affixed to a patient 704. The patient worn sensor further includes a sensor housing 710. The sensor housing 710 can include electrical components for processing signals received from and detected in association with the patient 704 and for transmitting the information to other computing devices. The sensor housing 710 can, for example have a design that is similar to or identical to the sensor housing 110 describe with respect to FIGS. 2-4. In the example shown, the sensor housing 710 is affixed to the main housing 712 (not shown) of the electrode assembly 700. The main housing 712 is affixed to a left upper chest portion of the patient 704 near the patient 704's heart. As previously described, in some implementations, the main body 712 includes two electrode connectors that connect to two single electrode pads affixed to the skin of patient 704. These two electrodes can serve as "left arm" leads for collecting vital sign information from the patient 704.

FIG. 8 additionally shows the electrode connectors 720a-b of the electrode lead 716 positioned on the right side of the patient 704's chest to serve as "right arm" leads. In the example shown, the electrode connectors 720a-b are operatively connected to electrode pads 724a-b respectively. The electrode pads 724a-b include electrodes for sensing patient vital signs and adhesive layers for affixing to the patient 704's skin. FIG. 8 further shows the electrode connector 722 of the electrical lead 718 positioned on a left side of the patient 704's abdomen to serve as a "left leg" lead. In the example shown, the electrode connector 722 is operatively connected to an electrode pad 724c. The electrode pad 724c includes an electrode for sensing patient vital signs and an adhesive layer for affixing to the patient 704's skin.

In some implementations, the patient worn sensor 702 includes a temperature sensor 706 that extends from the sensor housing 710 to underneath the patient 704's armpit for monitoring, tracking, and recording body temperature for the patient 704. The temperature sensor 706 can include both reusable portions and temporary/disposable portions. For example, the temperature sensor 706 can include a disposable contact (such as a "red dot" ECG electrode pad) for affixing to the patient 704's skin under the patient 704's armpit. The temperature sensor 706 can, for example, further include permanent portions that include temperature sensing portions, circuitry for interpreting and processing temperature data received from the patient, and a cable running from the main body of the patient worn sensor 702 around the chest of the patient 704 to the patient 704's armpit. In some implementations, rather than including functionality for interpreting temperature data collected from the patient 704, the temperature sensor 706 can collect raw data that is processed by circuitry contained within the sensor housing 710 of the patient worn sensor 702 or other computing devices in communication with the patient worn sensor 702.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination. Moreover, the separation of various system components in the embodiments described above should not be understood as requiring such separation in all embodiments.

Thus, particular embodiments of the subject matter have been described. Other embodiments are within the scope of the following claims. In some cases, the actions recited in the claims can be performed in a different order and still achieve desirable results.

What is claimed is:

1. A patient monitoring device for use with an electrode assembly configured to be applied to the skin of a patient, the device comprising:
   an electronics assembly having one or more extending contacts, each of the one or more extending contacts configured to releasably couple to an electrode of the electrode assembly; and
   one or more stabilizing boots, each of the one or more stabilizing boots encircling one of the one or more extending contacts;
   wherein each of the one or more stabilizing boots is configured to allow for a greater degree of movement in a Z-axis direction than in X-axis and Y-axis directions of the electronics assembly relative to the patient.

2. The device of claim 1, wherein each of the one or more stabilizing boots at least partially encircles a portion of an electrode of the electrode assembly when the device is coupled to the electrode assembly.

3. The device of claim 1, wherein the one or more stabilizing boots comprises a first stabilizing boot being equidistantly encircled by four other stabilizing boots.

4. A patient monitoring device for use with an electrode assembly configured to be applied to the skin of a patient, the device comprising:
   an electronics assembly having one or more extending contacts, each of the one or more extending contacts configured to releasably couple to an electrode of the electrode assembly; and
   one or more stabilizing boots, each of the one or more stabilizing boots encircling one of the one or more extending contacts;
   wherein the one or more stabilizing boots comprises at least two stabilizing boots; and
   wherein the one or more stabilizing boots comprises a first stabilizing boot constructed of a material having a higher level of rigidity than the other stabilizing boots of the one or more stabilizing boots.

5. The device of claim 4, wherein the first stabilizing boot has a substantially central position relative to the other stabilizing boots of the one or more stabilizing boots.

6. The device of claim 4, wherein the first stabilizing boot restricts movement of the sensor assembly relative to the patient in a Z-axis direction to a greater degree than the other stabilizing boots of the one or more stabilizing boots.

7. The device of claim 4, wherein the one or more stabilizing boots comprises five stabilizing boots, with the first stabilizing boot being equidistantly encircled by four other stabilizing boots.

8. The device of claim 4, wherein each of the one or more stabilizing boots is configured to allow for a greater degree of movement in a Z-axis direction than in X-axis and Y-axis directions of the electronics assembly relative to the patient.

9. The device of claim 8, wherein the first stabilizing boot restricts movement of the sensor assembly relative to the patient in the Z-axis direction to a greater degree than the other stabilizing boots of the one or more stabilizing boots.

10. The device of claim 4, wherein each of the one or more stabilizing boots at least partially encircles a portion of an electrode of the electrode assembly when the device is coupled to the electrode assembly.

11. The device of claim 4, wherein each of the one or more stabilizing boots at least partially encircles a portion of an electrode of the electrode assembly when the device is coupled to the electrode assembly.

12. The device of claim 4, wherein each of the one or more stabilizing boots is configured to contact a surface of the electrode assembly.

13. The device of claim 12, wherein the surface of the electrode assembly is the surface of an elastic layer of the electrode assembly.

14. The device of claim 12, wherein the surface of the electrode assembly comprises:
   an elastic layer that is substantially larger along an X-axis and a Y-axis in comparison to a Z-axis of the elastic layer;
   a plurality of electrodes, a portion of each electrode of the plurality of electrodes extending at least partially through the elastic layer; and
   a stabilizing sheet positioned between at least a portion of each electrode and the elastic layer, the stabilizing sheet configured to restrict movement of the plurality of electrodes relative to each other along the direction of the X-axis and the direction of the Y-axis;
   wherein a portion of each electrode extends through the stabilizing sheet.

15. The device of claim 14, wherein the surface of the electrode assembly is the surface of the stabilizing sheet.

16. The device of claim 14, wherein the one or more stabilizing boots are configured to absorb shock caused by motion of the electrodes of the electrode assembly.

17. The device of claim 14, wherein the one or more stabilizing boots are configured to absorb motion caused by flexing of the elastic layer as the elastic layer moves in response to movement of a patient's skin.

18. The device of claim 4, wherein the one or more stabilizing boots are configured to absorb shock caused by motion of a patient to which the electrode assembly is affixed.

19. The device of claim 4, further comprising a sensor housing that encases at least a portion of the electronics assembly;
   wherein the one or more stabilizing boots is formed using an over molding process and wherein the one or more stabilizing boots are integrated with a portion of the sensor housing as an integral piece.

20. The device of claim 4, wherein each of the one or more stabilizing boots has a height of between about 4 mm and about 6 mm and an outer circumference of between about 13 mm and about 16 mm.

* * * * *